(12) United States Patent
Guralnik et al.

(10) Patent No.: US 9,017,253 B2
(45) Date of Patent: Apr. 28, 2015

(54) SYSTEM FOR BODY ACCESS HAVING ADJUSTABLE DIMENSIONS

(75) Inventors: Mordechai Guralnik, Irvine, CA (US); Martin Goldstein, Teaneck, NJ (US); Avi Barak, Teaneck, NJ (US)

(73) Assignee: Amplifico, LLC, Irvine, CA (US)

( * ) Notice: Subject to any disclaimer, the term of this patent is extended or adjusted under 35 U.S.C. 154(b) by 202 days.

(21) Appl. No.: 13/698,666

(22) PCT Filed: May 18, 2011

(86) PCT No.: PCT/US2011/036987
§ 371 (c)(1),
(2), (4) Date: Nov. 19, 2012

(87) PCT Pub. No.: WO2011/146608
PCT Pub. Date: Nov. 24, 2011

(65) Prior Publication Data
US 2013/0066157 A1 Mar. 14, 2013

Related U.S. Application Data

(60) Provisional application No. 61/353,394, filed on Jun. 10, 2010, provisional application No. 61/345,861, filed on May 18, 2010.

(51) Int. Cl.
| | | |
|---|---|---|
| A61B 1/32 | (2006.01) | |
| A61B 17/34 | (2006.01) | |
| A61B 17/02 | (2006.01) | |
| A61B 17/00 | (2006.01) | |
| A61B 19/00 | (2006.01) | |

(52) U.S. Cl.
CPC ......... *A61B 17/3439* (2013.01); *A61B 17/0218* (2013.01); *A61B 17/34* (2013.01); *A61B 17/3421* (2013.01); *A61B 17/3431* (2013.01); *A61B 2017/00407* (2013.01); *A61B 2017/00557* (2013.01); *A61B 2017/00685* (2013.01); *A61B 2017/00867* (2013.01); *A61B 2017/00876* (2013.01); *A61B 2017/3433* (2013.01); *A61B 2017/345* (2013.01); *A61B 2019/4836* (2013.01)

(58) Field of Classification Search
USPC .................................................. 600/206, 208
See application file for complete search history.

(56) References Cited

U.S. PATENT DOCUMENTS

| | | | |
|---|---|---|---|
| 4,984,564 A | * | 1/1991 | Yuen .............................. 600/207 |
| 5,176,659 A | | 1/1993 | Mancini |
| 5,183,464 A | | 2/1993 | Dubrul et al. |
| 5,447,503 A | | 9/1995 | Miller |
| 5,944,691 A | | 8/1999 | Querns et al. |
| 2001/0012950 A1 | * | 8/2001 | Nishtala et al. ............... 606/198 |
| 2002/0045914 A1 | | 4/2002 | Roberts et al. |
| 2002/0123765 A1 | | 9/2002 | Sepetka et al. |
| 2006/0069404 A1 | | 3/2006 | Shluzas et al. |
| 2006/0235458 A1 | | 10/2006 | Belson |
| 2008/0200943 A1 | | 8/2008 | Barker et al. |

* cited by examiner

*Primary Examiner* — Andrew Yang
(74) *Attorney, Agent, or Firm* — JMB Davis Ben-David

(57) ABSTRACT

A device including a hollow pipe with a variable diameter is used for medical procedures. Means are provided for reducing the diameter either internally or externally so that the pipe can be inserted into a patient's body through an incision or an opening until the distal end of the pipe reaches a desired position. Thereafter, the diameter of the pipe is increased to allow various surgical devices to be introduced through the pipe.

2 Claims, 17 Drawing Sheets

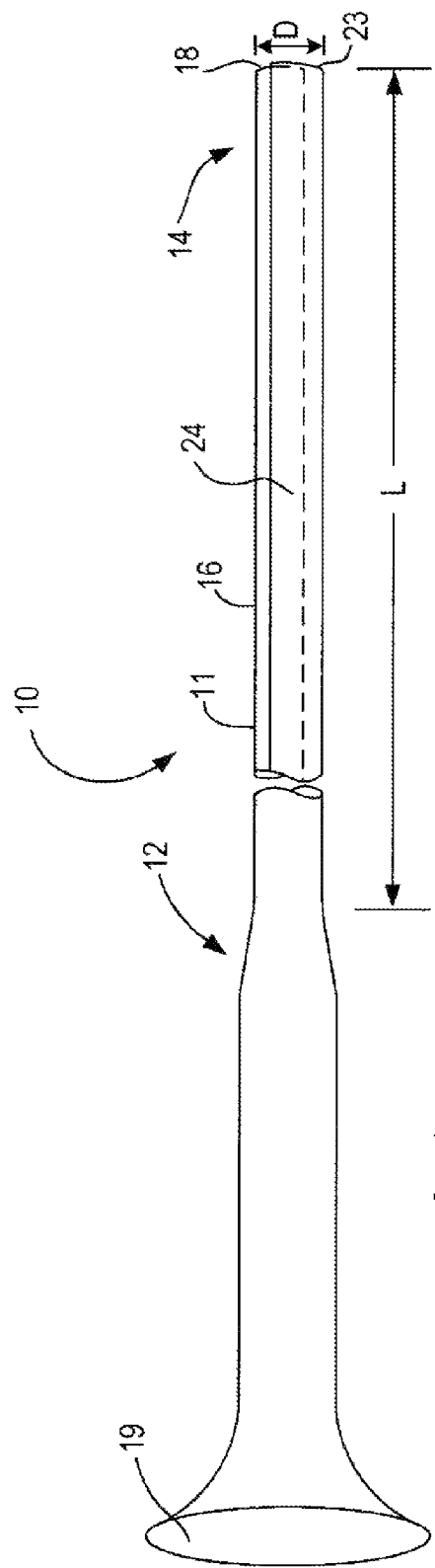
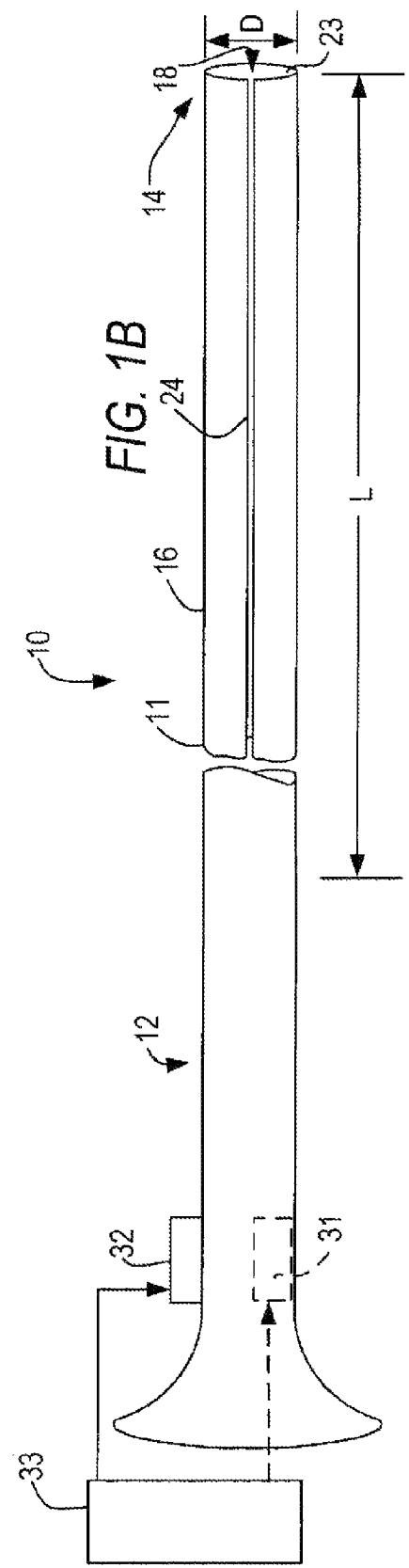

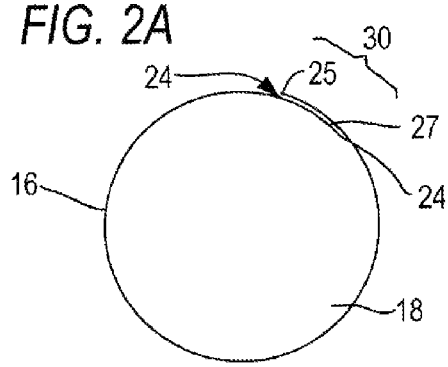
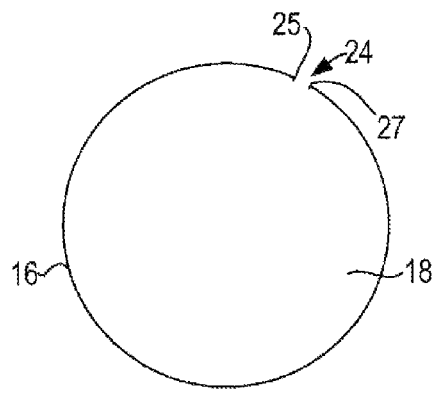
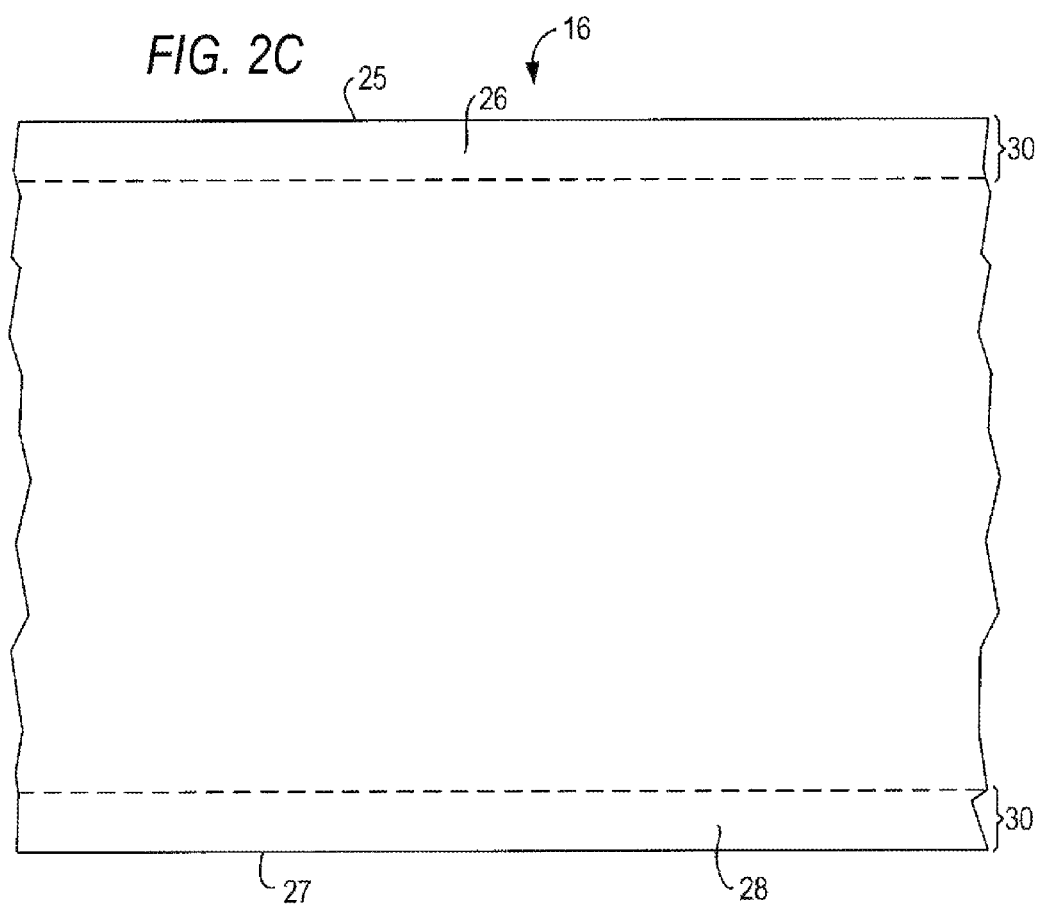

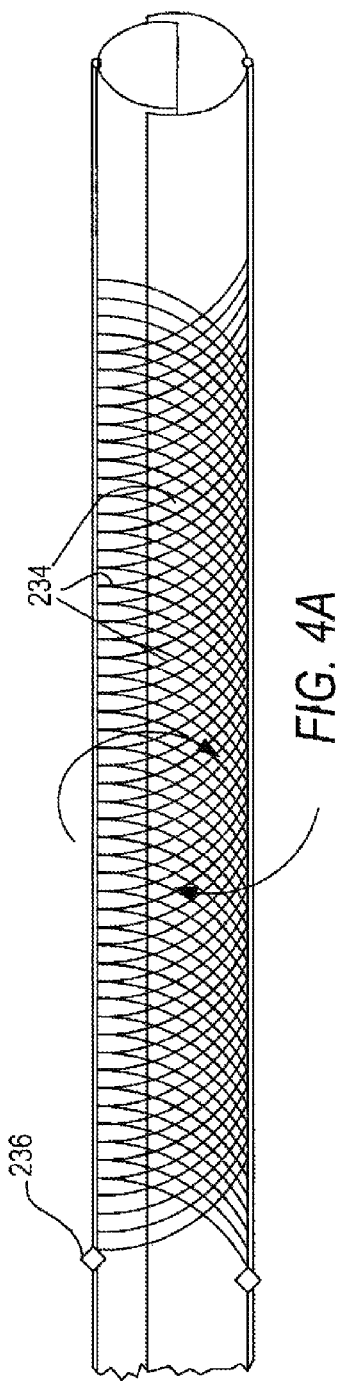
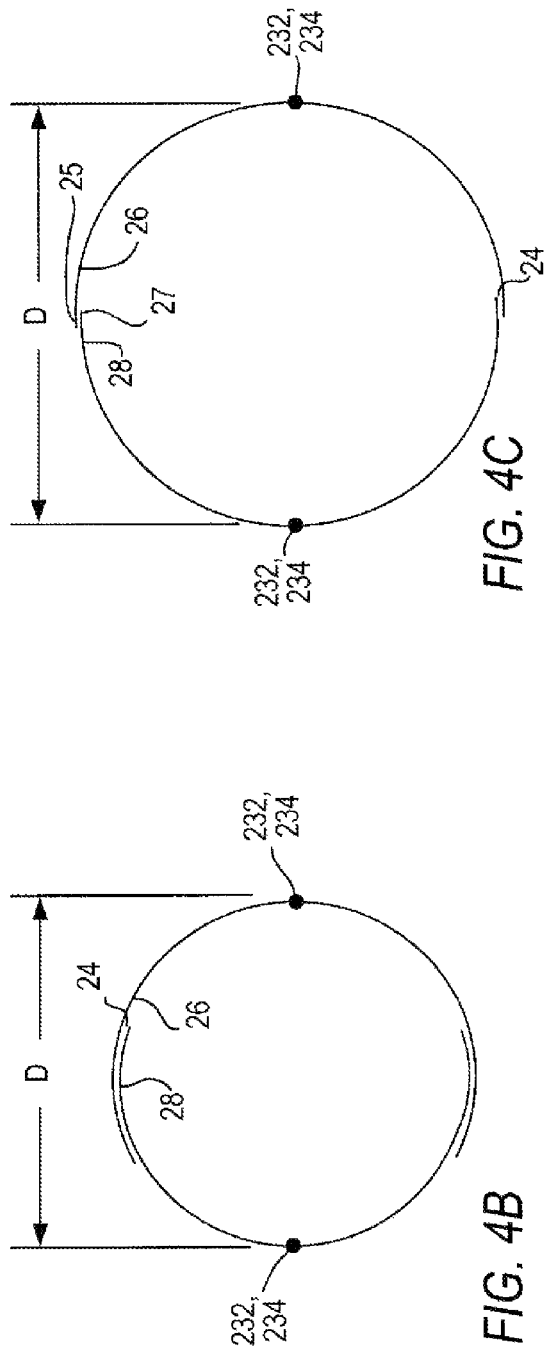
FIG. 4A
FIG. 4B
FIG. 4C

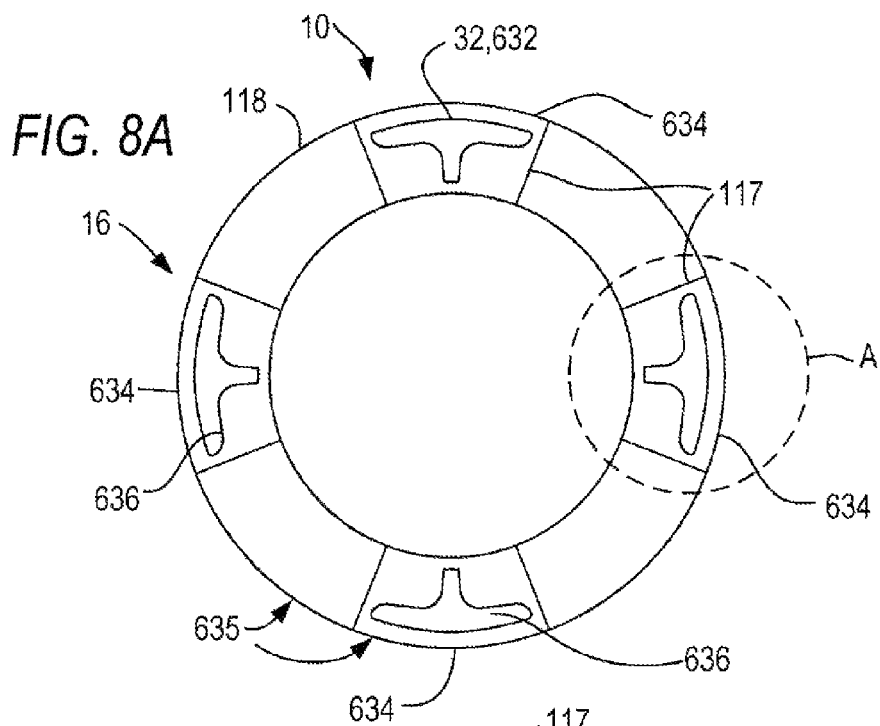
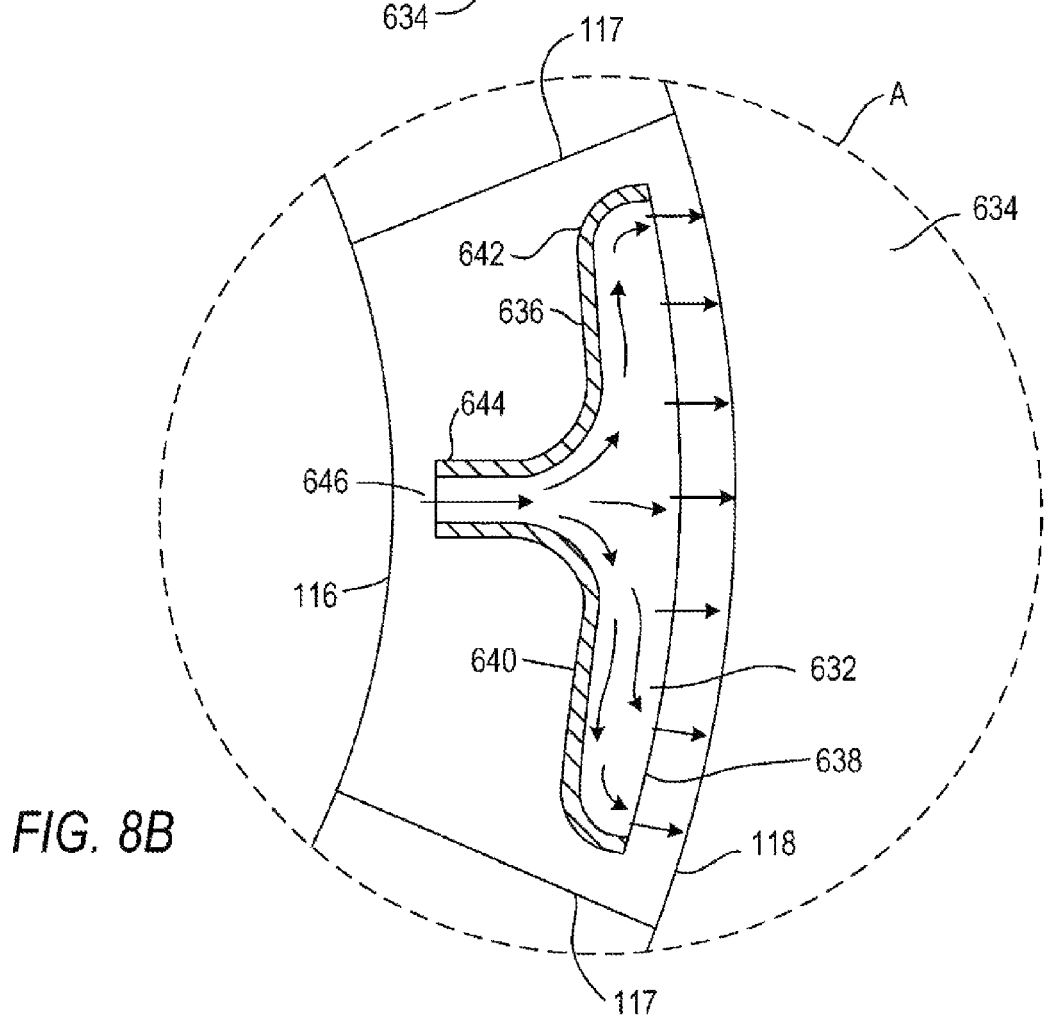

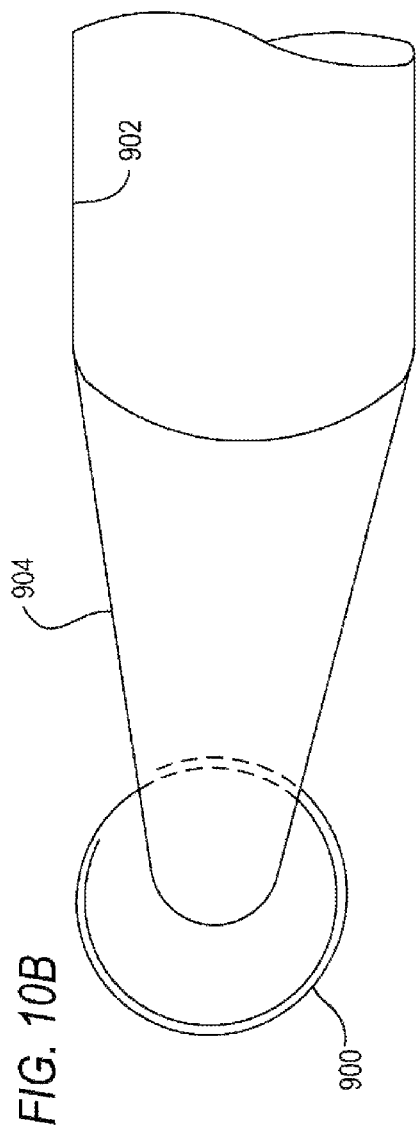
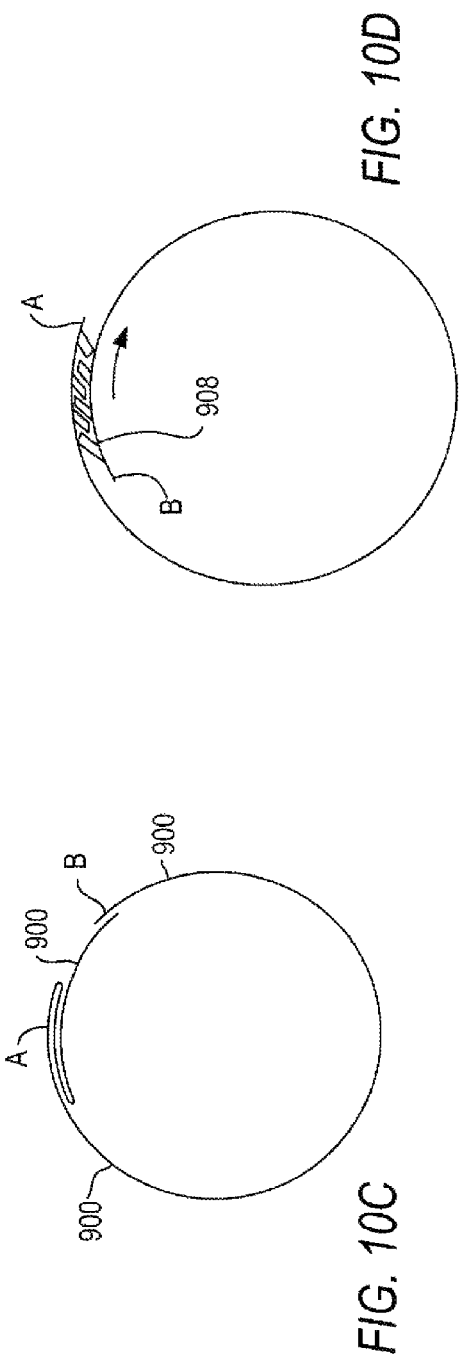
FIG. 10B
FIG. 10C
FIG. 10D

SYSTEM FOR BODY ACCESS HAVING ADJUSTABLE DIMENSIONS

RELATED APPLICATIONS

This is the U.S. National Stage of International Application No. PCT/US2011/036987, filed May 18, 2011, which was published in English under PCT Article 21(2), which in turn claims the benefit of U.S. Provisional Patent Application No. 61/345,861 filed May 18, 2010 and U.S. Provisional Patent Application No. 61/353,394 filed Jun. 10, 2010, which are incorporated by reference.

FIELD OF THE INVENTION

The present invention relates to a system for accessing a body cavity by creation of an access channel and by providing radial expansion of small diameter access channels.

BACKGROUND OF THE INVENTION

Interventional procedures which provide access to body cavities have varied applications for various medical indications. For example, ureteroscopy is often performed using a ureteral access sheath. The small diameter of ureters presents a challenge when attempting to insert an access sheath that is small enough to insert without damaging the ureter and large enough to pass surgical instruments or other objects through to and from the bladder. Other examples of applications which require access to body cavities include intubations, percutaneous procedures, vascular procedures, procedures for the gastrointestinal tract, reproductive tract, lymphatic system or others.

An access pathway may be created through a natural channel in the body, or may be artificially created, depending on the procedure or indication.

Frequently, an access system cannot be easily introduced through a urinary system or other vessels, due to tortuosity in the vessel, strictures within the vessel, or other causes. More particularly, systems which have diameters sufficient to treat the vessel or organ may be too large to pass through problematic areas within the body or body lumen. Systems which can be introduced in a contracted state, and later expanded when within the body, have been developed.

A commonly known technique for enlarging an initial access puncture involves successively introducing larger diameter rods through the access hole and into the internal organ. Systems designed to minimize trauma associated with such techniques include the use of an outer sheath which is radially expandable through various methods. An example of such a system is disclosed in U.S. Pat. No. 5,183,464 to Dubrul et al, entitled "Radially Expandable Dilator." The dilation tube, or access sheath, is radially expandable from a small diameter to a larger diameter by axial insertion of an expansion member through the axial lumen of the dilation tube.

This system is useful for expanding a puncture site and does not require a contraction to retract the dilator from the body. A catheter for insertion into vasculature is disclosed in U.S. Pat. No. 5,944,691 to Querns et al. This catheter is designed with stripes of rigid material and stripes of expandable material, wherein an expanding member inserted through the catheter causes the catheter to irreversibly expand in the radial direction.

An example of an expandable medical access sheath is disclosed in US Patent Publication 2008/0200943. An elongate tubular member is made of expandable material which can be folded when in its contracted state. The sheath is then expanded by introduction of a dilator through the lumen of the sheath. The material has a first configuration which is collapsed, and a second configuration which is enlarged and which includes elements or structures within the sheath which resist re-collapse. However, pressure within the vessel may cause the sheath to collapse due to the generally flexible nature of the material.

It would therefore be beneficial to have a system and method for accessing a vessel in the body which has a variable diameter, which can be contracted for removal from the vessel, and which will maintain rigidity when open in the vessel.

SUMMARY OF THE INVENTION

These needs are addressed by the present invention which comprises in one aspect a tube formed by rolling a sheet of spring-like flexible material onto itself to form an access sheath which is configured and adapted to be inserted in a lumen such as a vessel in a body. The resulting tube has a diameter which can be expanded when a hollow pipe of greater external diameter than the internal diameter of the tube is inserted in the tube, thereby causing the coiled sheath to uncoil slightly and expand the internal diameter. The tube is also adapted to coil by the sheath rolling back into itself when the pipe is extracted; the tube can then be easily removed from the lumen.

In some embodiments, the sheath has a tooth-like locking device which can lock the tube at different diameters. After the pipe has forced the tube to be expanded (by uncoiling the sheath), and the pipe is extracted, the expanded diameter does not return to its original diameter until the tooth-like locking device is pulled out. Pulling out the tooth-like locking device causes the sheath to collapse back into its original rolled state, thereby allowing it to be easily extracted.

In other embodiments, the access sheath includes a bar attached to strategically spaced hinges connecting it to legs, which are in turn attached to sliding bars running parallel to the inside of the access sheath and are equipped with stoppers which stop them from moving forward. In these embodiments, the inner bar can be pushed, which causes the legs to change angle within the access sheath, thereby causing the sliding bars to move away from each other and the spring to open. Once the spring is locked in place, the entire opening mechanism is able to be extracted so that tools can be easily inserted and removed into the access sheath tube. The tooth-like locking device can be pulled out independently of the access sheath, in which case the sheath to collapse into its original rolled space (having the smallest diameter), thereby permitting the sheath to be easily extracted.

BRIEF DESCRIPTION OF THE DRAWINGS

The above and further advantages of the present invention may be better understood by referring to the following description in conjunction with the accompanying drawings in which:

FIGS. 1A and 1B are schematic illustrations of a system in a first configuration and a second, expanded configuration, respectively, in accordance with embodiments of the present invention;

FIGS. 2A-2C are cross sectional illustrations of the system of FIG. 1A in a collapsed configuration and FIG. 1B in an expanded configuration, respectively, in accordance with embodiments of the present invention;

FIGS. 4A-4C are schematic illustrations of the system of FIGS. 1A and 1B, in accordance with another embodiment of the present invention;

FIGS. 8A and 8B are a cross-sectional view and a close-up cross-sectional view, respectively of the system of FIGS. 1A and 1B in accordance with additional embodiments of the present invention;

FIG. 10B is a schematic view of the access tube in a closed, rolled state and an expansion pipe about to be inserted;

FIG. 10C is a side, perspective view of an embodiment of the tube with a first locking device;

FIG. 10D is a side, perspective view of an embodiment of the tube with a second locking device having teeth;

DETAILED DESCRIPTION OF THE INVENTION

Figure 3B:
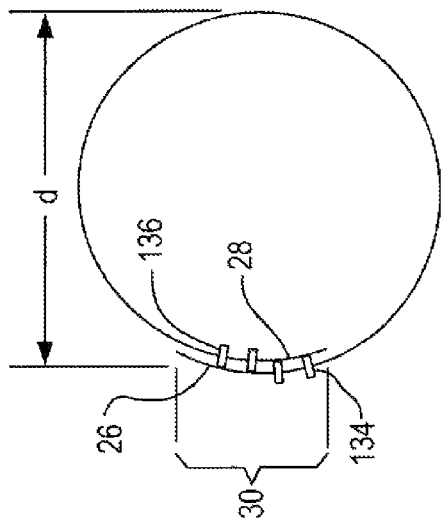
FIGS. 3A-3C are illustrations of the expandable body of the system of FIGS. 1A and 1B, shown in perspective view, and in cross-sectional views, in a contracted configuration and an expanded configuration respectively, in accordance with one embodiment of the present invention.

The present invention relates to a system and method for the purpose of performing a percutaneous procedure via an access channel. Before explaining the embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale. As used herein, an element or step recited in the singular and preceded with the word "a" or "an" should be understood as not excluding plural elements or steps, unless such exclusion is explicitly recited. In the following detailed description, numerous specific details are set forth in order to provide a thorough understanding of the present invention.

It will be understood by those of ordinary skill in the art that the present invention may be practiced without these specific details. In other instances, well-known methods, procedures, components and structures may not have been described in detail so as not to obscure the present invention. The principles and operation of a system and method according to the present invention may be better understood with reference to the drawings and accompanying descriptions.

Reference is now made to FIGS. 1A and 1B, which are schematic illustrations of a system 10 in a first configuration and a second, expanded configuration, respectively. It should be understood that the system 10 is generic to all the other embodiments shown in the remaining figures, unless otherwise noted. In embodiments of the present invention, system 10 forms an access sheath for providing access to a body lumen or organ, such that upon deployment of system 10, procedures may be performed on the body lumen or organ via insertion and/or removal of objects through the access sheath. System 10 includes an elongate member 11 having a proximal end 12, a distal end 14 and an expandable body 16 having a length L extending at least partway from proximal end 12 to distal end 14. Expandable body 16 includes at least a portion of elongate member 11, and in some embodiments, may extend the entire length of elongate member 11. In some embodiments, expandable body 16 may have different sections along its length with variable expansion capacities, as will be described further herein below.

Expandable body 16 has at least two configurations, wherein in a first configuration, expandable body 16 has a smaller outer diameter d, as shown in FIG. 1A, and in a second configuration, expandable body 16 has a larger outer diameter D, as shown in FIG. 1B. It should be noted that throughout the present application, drawings are not to scale and are for illustration purposes only. For the purposes of the present invention, "first" and "second" are not indications of an order of operation, but are merely used to designate two different configurations. In some embodiments, the first configuration may be implemented before the second configuration, while in other embodiments, the first configuration may be implemented after the second configuration. Moreover, switching between configurations may be possible as well. In addition, any number of intermediate configurations is possible as well, wherein each intermediate configuration has a different diameter. The change in diameter from a contracted to an expanded state varies in accordance with the particular application. For example, in a urological application, the contracted body 16 may have an outer diameter of approximately 2-3 French, while the expanded body may have an outer diameter as large as 15 to 20 French. For an intubation, the contracted body may have an outer diameter of 2 mm and an expanded body may have an outer diameter of 20 mm, in some embodiments, and up to 40 mm in other embodiments.

Elongate member 11 has a lumen 18 extending therethrough which is configured for receiving devices for accessing the vessel, such as, for example, guidewires, sensor devices, pharmaceutical delivery devices, or any other access or treatment devices. Lumen 18 is further configured for removing items from within the vessel, such as, for example, debris, blood, foreign objects, or any other item which may be removable from a vessel. Lumen 18 extends from proximal end 12 until distal end 14. A hub 19 is positioned at proximal end 12. Hub 19 is coupled to elongate member 11, providing access to lumen 18 from outside of the treatment site or body. Hub 19 may include external control components 32 for controlling expansion and contraction of expandable body 16, as will be described in further detail herein below. A distal opening 23 at distal end 14 of elongate member 11 provides access from lumen 18 to an internal site for treatment or access.

In accordance with embodiments of the present invention, the capacity for multiple configurations, each with a different diameter, is obtained by the use of at least one seam 24 and overlappable portions, as will be described in further detail.

Reference is now made to FIG. 2A and FIG. 2B, which are cross sectional illustrations of system 10 as shown in FIG. 1A in a collapsed configuration and FIG. 1B in an expanded configuration, respectively, in accordance with embodiments of the present invention. As shown in FIG. 2A, expandable body 16 has a seam 24 running longitudinally along its length. Seam 24 divides expandable body 16 into two sides, with a first side having a first longitudinal edge 25 and a second side having a second longitudinal edge 27. Reference is now made to FIG. 2C, which is an illustration of expandable body 16 in a flat configuration. As shown in FIG. 2C, a first overlappable portion 26—depicted until the dotted line—extends transversely from first longitudinal edge 25, and a second overlappable portion 28—also depicted by a dotted line—extends transversely from second longitudinal edge 27. In practice, expandable body 16 is used in a closed or semi-closed substantially tubular configuration, wherein first and second longitudinal edges 25 and 27 are in contact or in close proximity to one another. First overlappable portion 26 and second overlappable portion 28 are configured to at least partially overlap one another in a contracted configuration, as shown in FIG. 2A, and to separate from one another in an expanded configuration, as shown in FIG. 2B. Dimensions of the diameter of lumen 18 thus depend on a width of each of first and second overlappable portions which are in overlapping contact with one another. This width is referred to herein as overlapping width 30, and may be fixed or variable. The larger the overlapping width 30, the smaller the diameter of lumen 18, and thus, the smaller the overall diameter of system 10. Thus, by controlling the overlapping width 30 of first and second overlappable portions 26 and 28, dimensions of system 10 may be controlled or adjusted as needed. It should be readily apparent from the descriptions herein that system 10 may thus be expanded or contracted as needed. For example, when inserted into a vessel, system 10 may be in a contracted state. Once in place, system 10 may be expanded. In one embodiment, the edges are sized and shaped so that they interlock when in the expanded position. For example, a separate element (not shown) may be provided having a longitudinal groove receiving the edges of the 25, 27. Finally, once the procedure is finished, system 10 may once again be contracted and removed from the vessel. For example, if an interlocking member is used, this interlocking member is first pulled out completely, thereby releasing the edges. The invention is not limited to the description included herein, and may further include other configurations of variably contracting and expanding states. Moreover, certain portions of system 10 may be configured to expand while other portions are configured to contract or remain the same. In some embodiments, multiple seams 24 may be provided, as will be described further herein below. Control of overlapping width 30 may be done with an overlap control mechanism 32, as described with reference to several different embodiments in FIGS. 3-9. The overlap control mechanism includes an internal control portion 31, positioned on or within expandable body 16, and an external control portion 33, located outside of expandable body 16, and configured to stay outside of the human body during operation. External control portion 33 may be positioned, for example, on or in hub 19 or at some other external location.

Figure 3C:
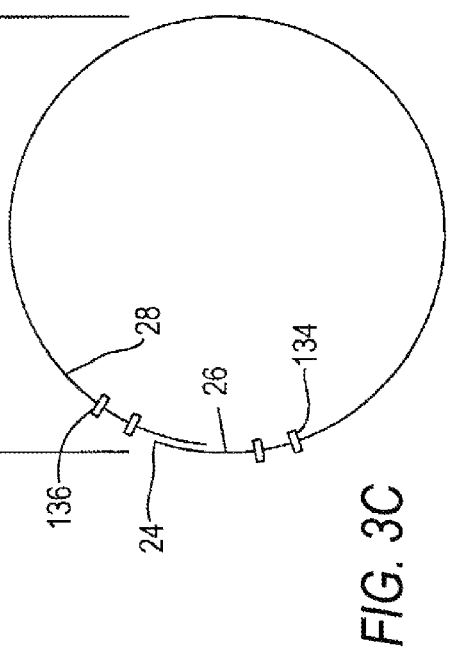
Figure 3A:
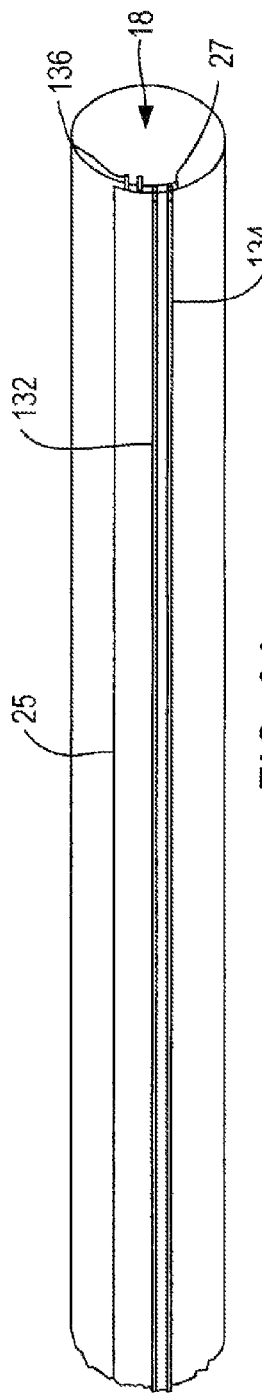

Reference is now made to FIG. 3A-3C, which are illustrations of expandable body 16 of system 10, shown in perspective view, and in cross-sectional views, in a contracted configuration and an expanded configuration respectively, in accordance with one embodiment of the present invention. Elongate body 16 includes seam 24, which forms first and second longitudinal edges 25 and 27. In some embodiments, two or more seams 24 may be present, which splits expandable body into two or more independent pieces. For the embodiment depicted in FIGS. 3A-3C, overlap control mechanism is a magnetic mechanism 132. Internal control portion 31 of magnetic mechanism 132 includes a first magnetic connector 134 positioned on or within first overlappable portion 26, and a second magnetic connector 136 positioned on or within second overlappable portion 28. First and second magnetic connectors 134 and 136 may be, for example, magnetic threads. First and second magnetic connectors 134 and 136 may extend fully or partially along length L of expandable body 16. In one embodiment, activation of first and second magnetic connectors 134 and 136 by application of an electrical charge causes a magnetic attraction between them, which causes first and second overlappable portions 26 and 28 to overlap one another, as shown in FIGS. 3A and 3B. This overlapping position is maintained for as long as activation is maintained. When activation is not maintained, expandable body 16 assumes its expanded configuration, wherein diameter D is larger, and overlappable portions 26 and 28 are separated, as shown in FIG. 3C. In another embodiment, activation of first and second magnetic connectors 134 and 136 by application of an electrical charge causes a magnetic repulsion—causing first and second overlappable portions 26 and 28 to be separated, as shown in FIG. 3C. This separate position is maintained for as long as activation is maintained. When activation is not maintained, expandable body 16 assumes its contracted configuration, wherein diameter d is smaller, and overlappable portions 26 and 28 are overlapping, as shown in FIGS. 3A and 3B. In some embodiments, multiple magnetic strands may be used, thus allowing for variable diameters. Thus, the diameter of system 10 may be increased or decreased incrementally depending on the number of strands that are negatively charged.

Expandable body 16 may be comprised of any suitable material, such as a rigid or semi-rigid material, including, for example, silicone, silicone-based materials, ceramic, carbon fiber reinforced materials, titanium or other bio-compatible metals, etc. In some embodiments, seam 24 may remain open. In other embodiments, such as upon introduction of fluids, for example, it may be necessary to close seam 24. This may be accomplished, for example, by provide a thin coating on or around expandable body 16, wherein the coating remains intact even though expandable body 16 has a seam or a gap. In some embodiments, a piece of fabric or other flexible type of material may be attached to each of longitudinal edges 25 and 27, wherein the material may fold or unfold, but will maintain an envelope around expandable body 16 for sealing purposes. Materials used for producing vascular grafts or other types of biocompatible mesh or cloth-like materials may be used.

External control portion 33 of magnetic mechanism 132 includes a source of electrical current, for example, switchable by a suitable electric switch and at least some of the magnets may be electric coils energized by the electric current.

Reference is now made to FIGS. 4A-4C, which are schematic illustrations of system 10, in accordance with one embodiment of the present invention. Expandable body 16 includes seam 24, which forms first and second longitudinal edges 25 and 27. In some embodiments, two or more seams 24 may be present, which splits expandable body into two or more independent pieces. For the embodiment depicted in FIGS. 4A-4C, overlap control mechanism 32 is a loop closure mechanism 232. Expandable body 16 is comprised of any material which can incorporate a wire mesh structure, such as, for example, a polymer, a metal, a composite or any other suitable material. Loop closure mechanism 232 includes a thread 234 woven or braided throughout expandable body 16. Thread 234 may be a metallic thread, such as a stainless steel or titanium ultra-thin thread. Alternatively, thread 234 may be another suitable material. Multiple threads 234 may be used. For example, when two independent pieces are present, a thread 234 may be included within each independent piece. A torquing mechanism 236 is positioned on expandable body 16, and may include one or multiple control knobs. Rotation of torquing mechanism 236 causes thread 234 to tighten or loosen, which causes expandable body 16 to contract or expand.

In some embodiments, seam 24 may remain open. In other embodiments, such as upon introduction of fluids, for example, it may be necessary to close seam 24. This may be accomplished, for example, by provide a thin coating on or around expandable body 16, wherein the coating remains intact even though expandable body 16 has a seam or a gap. In some embodiments, a piece of fabric or other flexible type of material may be attached to each of longitudinal edges 25 and 27, wherein the material may fold or unfold, but will maintain an envelope around expandable body 16 for sealing purposes. Materials used for producing vascular grafts or other types of biocompatible mesh or cloth-like materials may be used. In one embodiment the body is made of two segments that have the cross-section of a curved arc, the segments being nested together so they overlap, at least partially. Rotating about a longitudinal axis using the torquing mechanisms causes one segment to rotate with the other until their respective edges abut or overlap to form a lumen.

Figure 5:
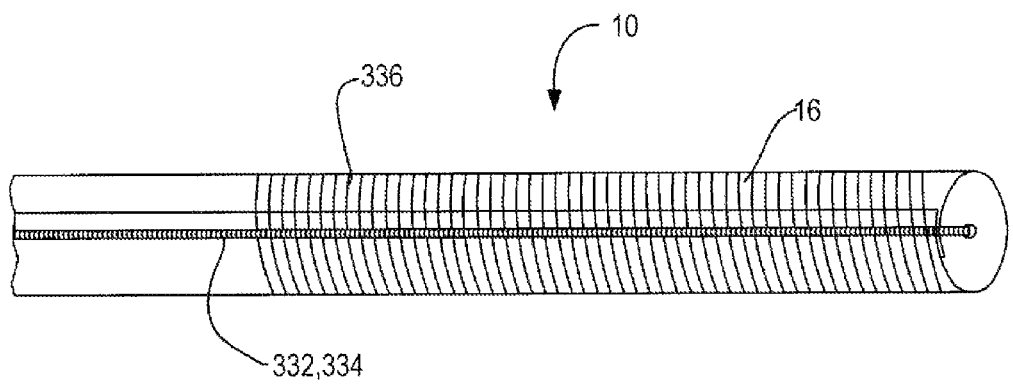
FIG. 5 is a perspective illustration of the system of FIGS. 1A and 1B in accordance with yet additional embodiments of the present invention.

Reference is now made to FIG. 5, which is a perspective illustration of system 10 in accordance with yet additional embodiments of the present invention. In this embodiment, overlap control mechanism is a screw mechanism 332. Screw mechanism 332 may be, for example, a threaded screw 334. Screw 334 is designed to be flexible along its length, but rigid in diameter, such that it does not inhibit insertion of system 10 into the body, but maintains its integrity during insertion and during the entire procedure. Screw mechanism 332 may be embedded within expandable body 16, for example, by placing screw 334 through a channel within expandable body 16. A thread 336 may also be placed through expandable body 16 or embedded therein, in a configuration which allows for body 16 to contract or expand upon turning of screw 334. For example, thread 336 may have a slinky configuration, wherein an angle of the slinky determines the number of rotations of screw 334 needed to expand or contract expandable body 16. Alternatively, the body 16 is made with diagonal slots (not shown) that engage the threads of the screw 336 in manner similar to a hose clamp.

Figure 6A:
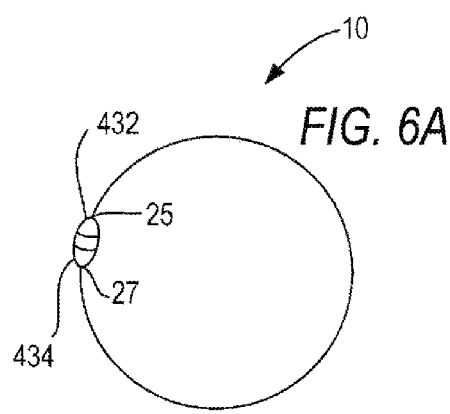
FIGS. 6a-C are schematic illustrations of the system of FIGS. 1A and 1B in accordance with yet additional embodiments of the present invention.
Figure 6B:
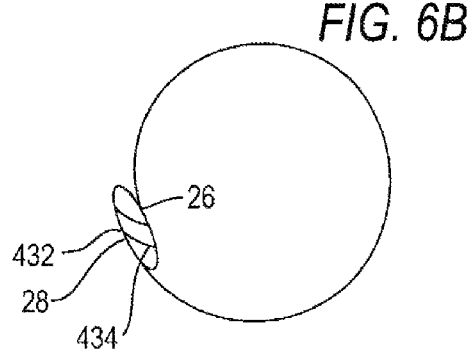
Figure 6C:
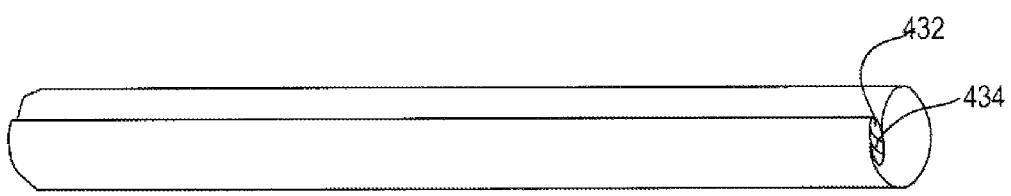

Reference is now made to FIG. 6, which is an illustration of system 10 in accordance with yet additional embodiments of the present invention. Overlap control mechanism 32 is an inflatable mechanism 432, including an inflatable portion 434 placed between longitudinal edges 25 and 27. Inflatable portion 434 extends along a length L of expandable body 16 to proximal hub 16. An inflation hub may be provided for providing fluid or air to inflatable portion 434. In a contracted configuration, inflatable portion 434 is uninflated, and may lie between overlappable portions 26 and 28. In an expanded configuration, inflatable portion 434 is inflated via inflation fluid through hub 19, causing inflatable portion to expand, thus separating overlappable portions 26 and 28 from one another.

Figure 7A:
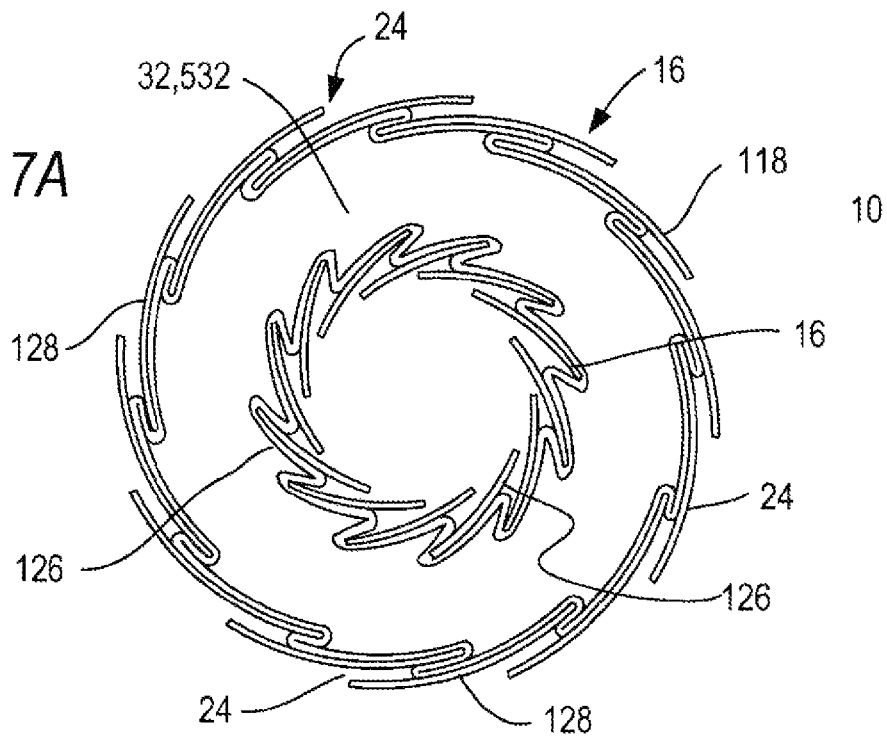
FIGS. 7A and 7B are cross-sectional illustrations of the system of FIGS. 1A and 1B in accordance with additional embodiments of the present invention.
Figure 7B:
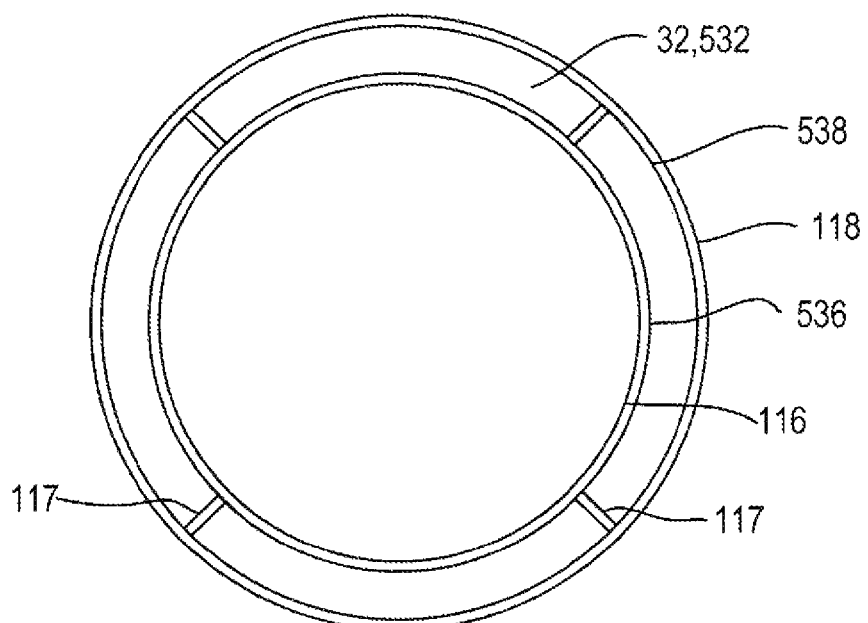

Reference is now made to FIGS. 7A-7B, which are cross-sectional illustrations of system 10 in accordance with additional embodiments of the present invention. Expandable body 16 comprises an inner expandable tube 116 and an outer expandable tube 118 which is coaxial to inner expandable tube 116. Inner and outer expandable tubes 116 and 118 are comprised of a rigid material such as a metal or composite. In some embodiments, outer expandable tube 116 is comprised of a more flexible material than inner expandable tube 118. This may be accomplished by using different materials for each of inner and outer expandable tubes 116 and 118, by treating one or the other or both of inner and outer expandable tubes 116 and 118 to change the material properties thereof, or by mechanical means. Mechanical means may include addition of certain elements, such as composite fibers, for example. Other mechanical means may include structural configurations of each of inner and outer expandable tubes 116 and 118. In some embodiments, connectors 117 are positioned between inner expandable tube 118 and outer expandable tube 116, connecting inner and outer expandable tubes 118 and 116 to each other. In one embodiment, connectors 117 are separators, wherein there is no possibility of substances passing from one compartment to the next. In other embodiments, connectors 117 are permeable or semi-permeable to fluid or other substances. Permeability may be accomplished either by choice of material, or by providing a woven or porous structure. In one embodiment, as depicted in FIG. 7A, only a single seam 24 may be incorporated into each of inner and outer expandable tubes 116 and 118, and expandable body 16 has a contracted and an expanded configuration similar to those described above with reference to FIGS. 3-6, but with both inner and outer expandable tubes having this configuration so that they can remain substantially coaxial.

In another embodiment, as shown in FIG. 7B, multiple seams 24 are incorporated into both inner and outer expandable tubes 116 and 118, thus forming multiple inner overlappable portions 126 and outer overlappable portions 128. Thus, longitudinal edges of inner overlappable portions 126 are in overlapping contact with one another in a contracted configuration, as shown in FIG. 7A, and are separated from one another (either partially or fully) in an expanded configuration so as to form a more cylindrical shape, as shown in FIG. 7B. Overlap control mechanism 32 is a circumferential inflatable mechanism 532. Circumferential inflatable mechanism includes a sealed flexible chamber 534 comprised of an inner wall 536 and an outer wall 538. Essentially, sealed flexible chamber 534 is similar to a balloon, and may be formed of any suitable material, such as silicone, for example. Sealed flexible chamber 534 is sandwiched between inner and outer expandable tubes 116 and 118 and runs longitudinally along expandable body 16. An inflation lumen is provided at proximal hub 19 of system 10 to provide air, gas, or other fluid into sealed flexible chamber 534 for expansion thereof. Upon expansion of sealed flexible chamber 534, outer expandable tube 118 expands outward, thereby increasing a diameter of outer expandable tube 118. Since inner expandable tube 116 is more rigid than outer expandable tube 118, when outer expandable tube 118 expands outward, inner expandable tube 116 is pulled along with it and also expands outward. Moreover, when connectors 117 are used, expansion of outer expandable tube 118 further pulls inner expandable tube in an outward direction. It is possible that during expansion of inner expandable tube 118 there will be some movement towards the inside of the lumen—that is, inner expandable tube 118 may be pushed in a direction wherein a diameter of inner expandable tube decreases slightly and wherein sealed flexible chamber 534 expands, pushing inner and outer expandable tubes in opposite directions. However, the tubes are designed such that outer expandable tube 116 is at least 2-3 times more flexible, and possibly even 4 or 5 times more flexible or even more than inner expandable tube 118, thereby minimizing such opposing effects. The embodiment shown in FIGS. 7A and 7B may be particularly suitable for larger applications such as intubations. Reference is now made to FIGS. 8A and 8B, which are cross-sectional illustrations of system 10, in accordance with yet additional embodiments of the present invention. Expandable body 16 comprises an inner expandable tube 116 and an outer expandable tube 118 which is coaxial to inner expandable tube 116. Inner and outer expandable tubes 116 and 118 are comprised of a rigid material such as a metal or composite. In some embodiments, outer expandable tube 116 is comprised of a more flexible material than inner expandable tube 118. This may be accomplished by using different materials for each of inner and outer expandable tubes 116 and 118, by treating one or the other or both of inner and outer expandable tubes 116 and 118 to change the material properties thereof, or by mechanical means. Mechanical means may include addition of certain elements, such as composite fibers, for example. Other mechanical means may include structural configurations of each of inner and outer expandable tubes 116 and 118. Connectors 117 are positioned between inner expandable tube 118 and outer expandable tube 116, connecting inner and outer expandable tubes 118 and 116 to each other. In one embodiment, connectors 117 are separators, wherein there is no possibility of substances passing from one compartment to the next. In other embodiments, connectors 117 are permeable or semi-permeable to fluid or other substances.

Permeability may be accomplished either by choice of material, or by providing a woven or porous structure. Similar to the embodiments described above with respect to FIGS. 7A and 7B, one or multiple seams (not shown) are incorporated into both inner and outer expandable tubes 116 and 118, thus forming one or more multiple inner overlappable portions 126 and outer overlappable portions 128. Thus, longitudinal edges of inner overlappable portions 126 are in overlapping contact with one another in a contracted configuration, and are separated from one another (either partially or fully) in an expanded configuration while remaining substantially coaxial.

Figure 9A:
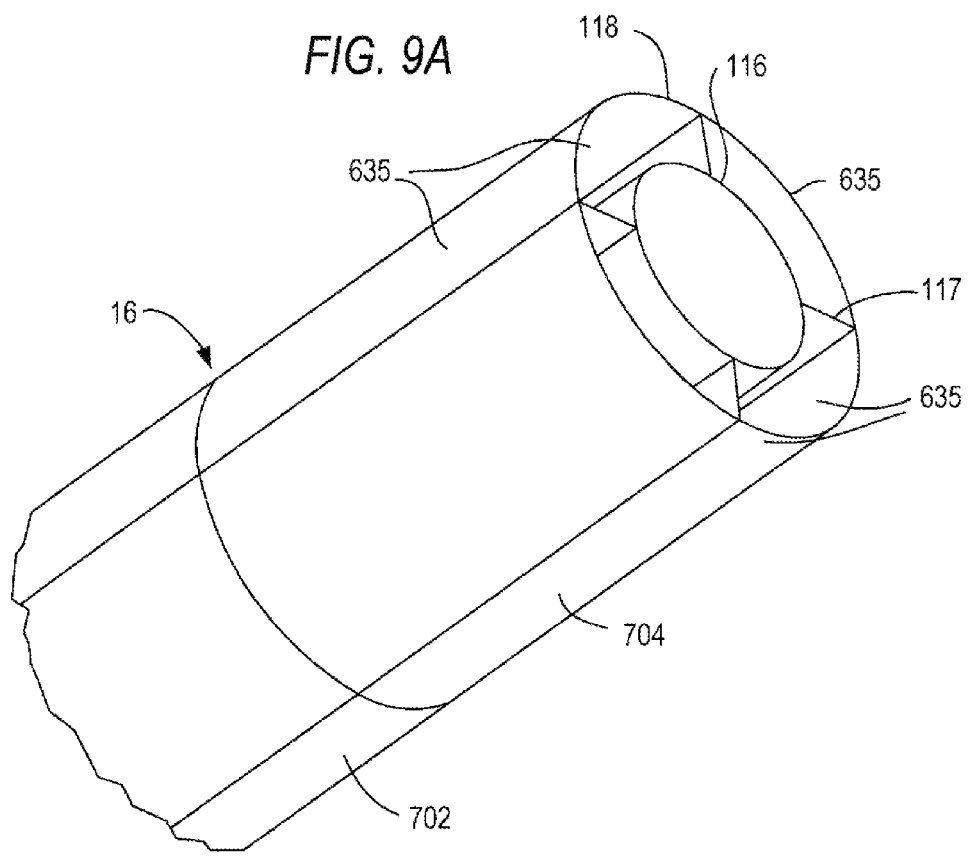
FIG. 9A is a perspective view of an expandable body of the system of FIGS. 7A-7B and 8A-8B, in accordance with an embodiment of the present invention.

Overlap control mechanism 32 is a compartmentalized inflatable mechanism 632. Circumferential inflatable mechanism includes multiple inflation chambers 634 separated from one another by connectors 117. Connectors 117 are situated circumferentially around expandable body 16, thus creating chambers 635 within a space between inner and outer expandable tubes 116 and 118. Connectors 117 may extend longitudinally along the length of expandable body 16, such that chambers 635 extend along a length of expandable body 16, as shown in FIG. 9A. In one embodiment, connectors 117 are separators, wherein there is no possibility of substances passing from one compartment to the next. In other embodiments, connectors 117 are permeable or semi-permeable to fluid or other substances. Permeability may be accomplished either by choice of material, or by providing a woven or porous structure. Chambers 635 may include two or more inflation chambers 634. In some embodiments, all of chambers 635 are inflation chambers 634. In other embodiments, only some of chambers 635 are inflation chambers 634, while others do not include an inflation component.

In most cases, it will be necessary to position inflation chambers 634 symmetrically around expandable member 16 so as to provide uniform expansion of expandable member 16. However, in certain applications it may be desirable to position inflation chambers 634 asymmetrically so as to provide different shapes for expandable member 16.

Reference is now made to FIG. 8B, which is an enlarged illustration of section A of FIG. 8A, showing an inflation chamber 634 in greater detail. Inflation chamber 634 includes an inflation element 636. Inflation element 636 includes an inlet 646, an outer segment 638, and an inner segment 640. Outer segment 638 is adjacent to or in contact with outer expandable tube 118, and inner segment 640 is close to inner expandable tube 116. Inlet 646 is a passage for fluid such as air, gas, or liquid, and leads directly into inflation element 636. Outer and inner portions 638 and 640 are connected to one another, thus forming a sealed element, wherein gas or liquid introduced through inlet 646 fill up a space created by outer and inner portions 638 and 640. Outer segment 638 is comprised of expandable material such as latex, or an elastic or elastomeric material, or a balloon-type of material such that upon filling with air or fluid, outer segment 638 is configured to expand or extend in an outward direction. Outer segment 638 extends along most or all of a length of a section of outer inflatable tube 116 which is included in the particular inflatable chamber 634 being described. Inner segment 640 is comprised of a more rigid material, such as titanium, stainless steel or any other rigid material. Inner segment 640 extends from edges of outer segment 638 (referred to herein as extended portion 642 of inner segment 640) towards inner expandable tube 116 (referred to herein as inward facing portion 644 of inner segment 640). Inward facing portion 644 leads directly into inlet 646. Thus, inner segment 640 is shaped such that inflation element 636 is relatively wide at its extended portion 642, which is adjacent to outer segment 638, and is relatively narrow at its inward facing portion 644, which is adjacent to inlet 646. Thus, inflation element 636 may take on a funnel or mushroom shape, for example. An inflation lumen is provided at a proximal end of system 10 to provide air, gas, or other fluid into inflation element 636. In one embodiment, a single inflation lumen is provided and is split into each of inflation elements 636, thus providing uniform inflation around a circumference of expandable body 16expandable body 16. In another embodiment, separate inflation lumens are provided to each of inflation elements 636, providing control over an amount of inflation of each of inflation elements 636.

Upon expansion of inflation elements 636, outer segments 638 expand outward, pushing against outer expandable tube 118, thereby increasing a diameter of outer expandable tube 118. Since inner segments 640 of inflation elements 636 are more rigid than outer segments 638, and since a surface area of outer segments 638 is larger than a surface area of inner segments 640, an outward force is created, pushing outer expandable tube 118 outward. Since inner expandable tube 116 is connected to outer expandable tube 118 by connectors 117, when outer expandable tube 118 expands outward, inner expandable tube is pulled along with it and also expands outward. The embodiment shown in FIGS. 8A and 8B may also be particularly suitable for larger applications such as intubations.

Figure 9B:
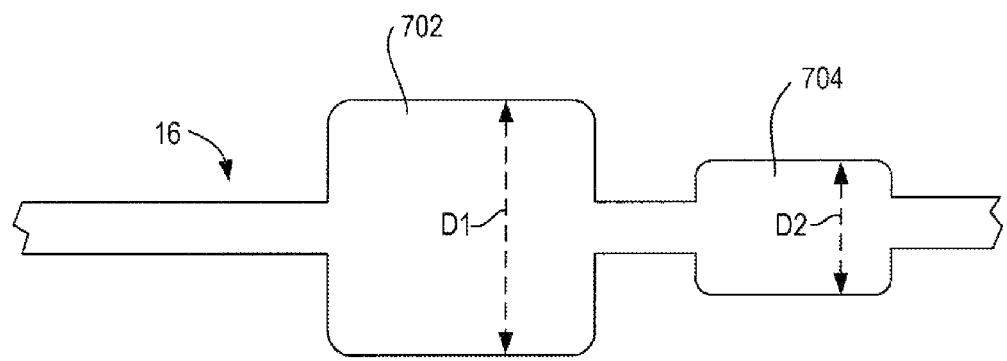
FIG. 9B is a schematic representation of the expandable body of FIG. 9A having varying diameters along its length.

Returning again to FIG. 9A, an additional feature is shown which may apply to either of the embodiments described above with respect to FIGS. 7A and 7B and 8A and 8B. As shown in FIG. 9A, expandable body 16 may be further compartmentalized in a longitudinal direction, such that separate sections (shown herein as 702 and 704) are formed along a length of expandable body 16. Each of the separate sections may be separately controllable in terms of expansion diameter. Thus, as shown in FIG. 9B, a first section 702 may be expandable to a first diameter D1 and a second section 704 may be expandable to a second diameter D2. This feature is not limited in the number of separate sections that may be used, and may be particularly useful for an application wherein different vessels of varying sizes are entered during a procedure. For example, in an ureteroscopy procedure, system 10 is configured to first enter a ureter, to pass through the bladder, into the urethra, and finally into the kidney. Each of these sections has a different anatomy and it would be advantageous to use a system such as the one described herein to adjust the expansion capacity as needed for each particular vessel or organ being entered. A set of radiopaque markers may be incorporated into expandable body 16 at the edges of each section so that the user can determine which section is in which location in the body at any given time. In some embodiments, expansion sensors may be included on each of the separate sections so that a reading of diameter and/or other expansion characteristics may be provided to the user. An example of such a sensor is a spiral-like metal sensor wrapped around the particular section of expandable body, and wherein separation of the spiral ends from one another signals an amount of expansion of that section. Other sensors are commonly known in the art, and any type of sensor which can convey this information may be used.

In both of the embodiments described above with respect to FIGS. 7A and 7B and FIGS. 8A and 8B, contraction of expandable body 16 is done by removing air or fluid via hub 19, which may in some cases be done with vacuum.

It is a particular feature of the present invention, that in all of the embodiments disclosed herein, the expanded configuration of system 10 maintains its rigidity or integrity, and thus, does not buckle under pressure from blood flow, vessel collapse, obstructions, or other causes.

Reference is now made to FIGS. 10A-10D which is a schematic illustration of another embodiment of the system In a first rolled configuration of this embodiment, shown in, perspective view, a tube is formed by rolling a sheet 900 of spring-like flexible material onto itself to form an access sheath which is configured and adapted to be inserted in a lumen such as a vessel in a body and the resulting tube has a diameter which can be expanded when a hollow pipe of greater external diameter than the internal diameter of the tube is inserted in the tube, thereby causing the coiled sheath to uncoils slightly and expand the internal diameter. The tube is also adapted to coil by the sheath rolling back into itself when the pipe is extracted, and the tube can then be easily removed from the lumen. A tool 902 with a conical tip 904 can be used to selectively expand the tube 904 after insertion.

Figure 10A:
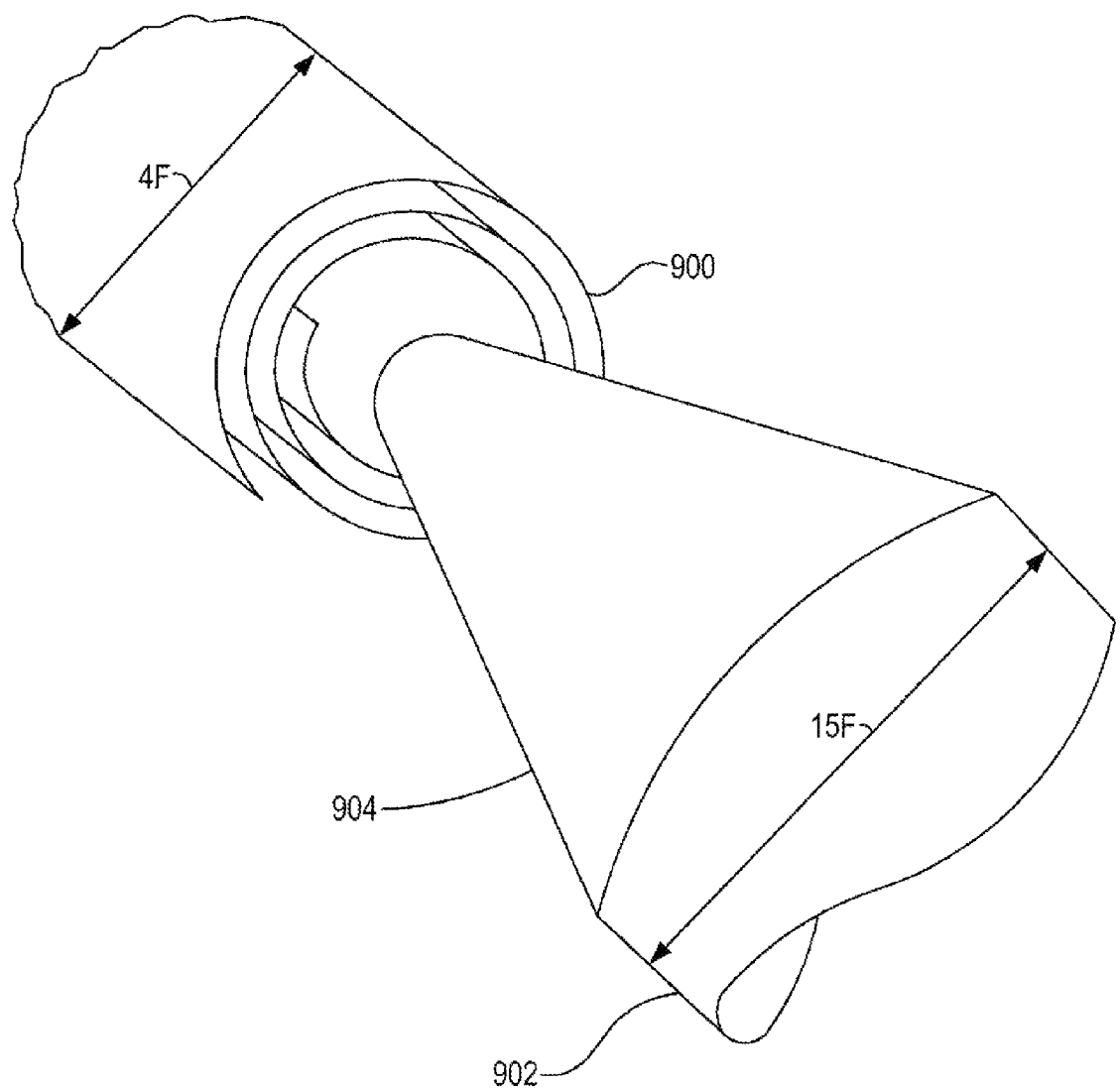
FIG. 10A is a schematic illustration of another embodiment of the system in a first rolled configuration, in perspective view.

FIG. 10C shows another embodiment in which the edges A and B of the sheet 900 are connected by an intermediate piece 906 to insure that they maintain their spacing, and therefore the sheet 900 maintains an expanded diameter. The intermediate piece can be inserted after the sheet has been opened by tool 902, and then removed, to allow the sheet to collapse to the configuration shown in FIG. 10A. In a version shown in more detail in FIG. 10D, sheath 900 has a tooth-like locking device 908 attached to each of the edges A and B which can lock the tube at different diameters. When the pipe is extracted (after it has forced the tube to be expanded by uncoiling the sheath), the expanded diameter does not return to its original diameter until the tooth-like locking devices is pulled out. This action causes the sheath to collapse back into its original rolled state, thereby allowing it to be easily extracted.

Figure 11:
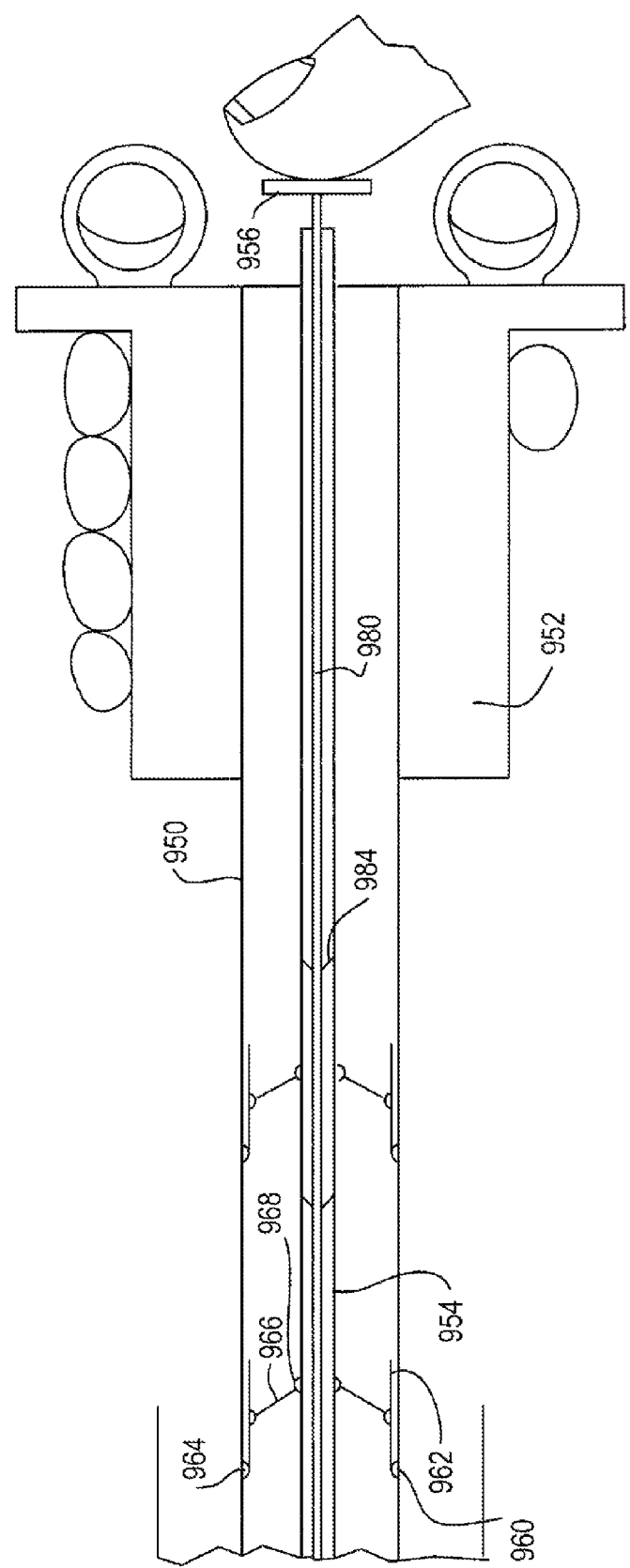
FIG. 11 is a cross-sectional view of an embodiment of the invention which includes the sliding bar used to expand the diameter of the access sheath when the plunger is pressed, and a pull ring locking mechanism, each being operated by a hand of an operator.

Another embodiment is shown in FIG. 11. In this embodiment, an access sheath 950 is formed of any suitable material as described and, has a first configuration in which the sheath 950 has a relatively small diameter. In this configuration, the sheath is inserted into a body cavity, such as the urethra, or through a proper incision to a body cavity or organ.

At one end, the sheath 950 is attached to a spreading mechanism that spreads the sheath 950 until its diameter increases to a new diameter. Once this new diameter is achieved, preferably the spreading mechanism is withdrawn and the appropriate locking mechanism is used to maintain the sheath in its expanded configuration until it is collapsed.

The spreading mechanism includes a handle 952 that is positioned near or is attached to the proximal end of sheath 950. The mechanism further includes a central member 954 selectively inserted through the sheath. The central member terminates with a thumb pad 956 and is longitudinally movable in sheath 950. At regular intervals along the central member 950 there are provided a plurality of expandable elements 960. Each element 960 includes a plurality of bars (from two to six bars per element) 964 extending longitudinally. Each bar is in intimate contact with the interior wall of the sheath 950. Each bar is connected to a hinged arm 966. Each arm is further connected by hinges 968 to the central member 954.

This embodiment operates as follows. Once the sheath 950 and central member 954 are in place and the bars 966 are in contact with the wall of sheath 950, the operator pushes the central member 954 forward using thumb pad 956 while holding handle 952 in place. This action causes the arms 966 to open radially outwardly thereby pushing against the internal wall of sheath 950 and causing the sheath to expand. A stopper 976 is used to limit how far the sheath is inserted. Once the sheath 950 is locked in its expanded position, the expansion member can be withdrawn. In an alternate embodiment, a wire 980 can be disposed inside the member 954 and provided with fingers 984 that move in position and force the hinges 968 to rotate, causing the arms to rotate outward. As previously mentioned, once the procedure is complete, the interlocking mechanism (such as teeth) are disengaged or opened, allowing the sheath to collapse to its smaller diameter configuration.

Figure 12:
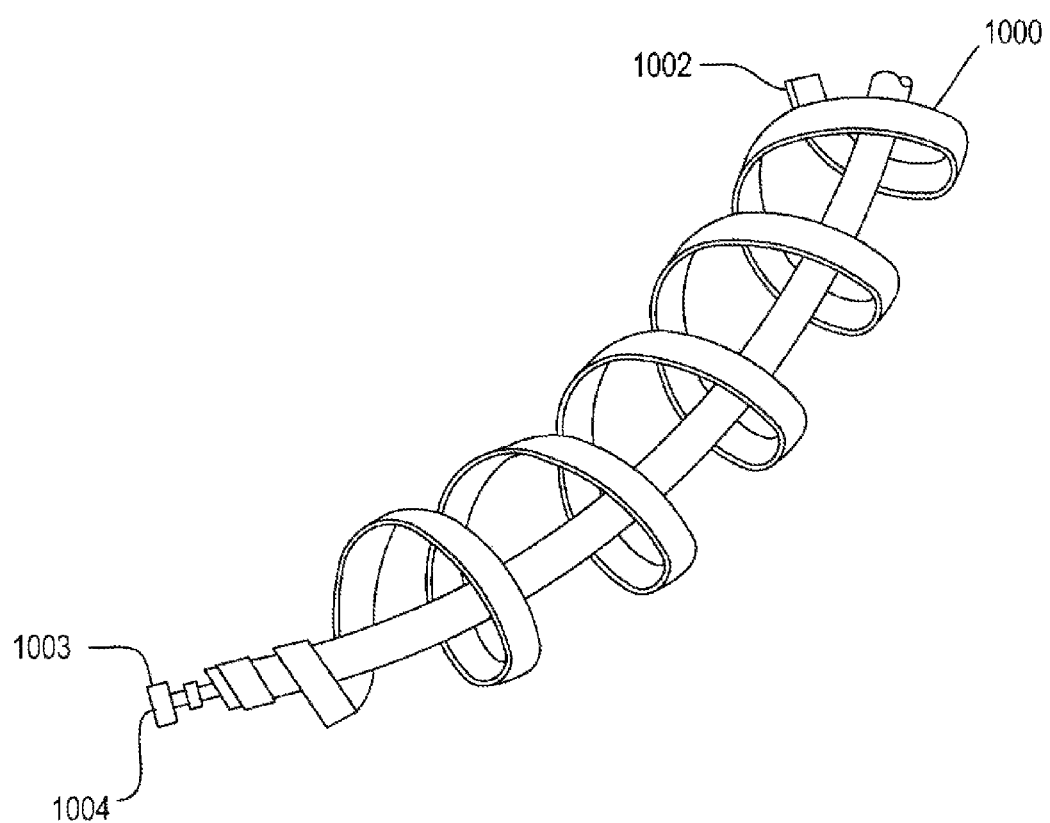
FIG. 12 shows a side elevational view of another embodiment wherein the body of the system includes a coil with a mechanism for selectively winding and unwinding the coil to decrease and increase its diameter.

Another embodiment is shown in FIG. 12. In this example, a spring type metal device 1000 is created using a flat wire shaped into a spring. Preferably a memory metal such as nitinol is used for the flat wire. Alternatively, a nitinol tube can be used, and a laser pattern can be cut into the tube, thus creating a memory spring-like structure. (Other similar material, such as a plastic having appropriate memory and strength characteristics may be used) The resting diameter of the tube can be the expanded or collapsed state.

Device 1000 includes a spring-like body 1002. It should be understood that the body 1002 is described as having a spring-like body 1002 only because it has the appearance of a spring. However, typically, a spring is primarily designed to compress and/or expand along the longitudinal axis to provide damping or biasing forces. In this case, the movement is along the horizontal axes of the "spring" like structure, specifically the diameter. The device 1000 is not made to be stretched or compressed along its longitudinal axis. The device has a resting state diameter that is either the contracted or the expanded diameter. In this case, a center wire/cable 1003 running up the length of the device, attached to the inside far end of the body 1002, locks on to it, then with a winding procedure, winds the spring down from the expanded diameter to the collapsed diameter. This allows for insertion and removal.

In an emergency case, the body can be "unscrewed" from the urethra and ureter, by manually turning the device, or using a hand crank.

The spring body 1002 has a silicone or rubber sleeve around it (not shown), which itself may be coated with a hydrophilic coating, which will facilitate the unscrewing from the urological tract. It will also protect the internal mucosa during this procedure. However, it is preferable to collapse the device prior to removal.

Typically, the body 1002 is made from a flat wire having a square or rectangular cross section with a thickness and height ranging from 0.025 mm to about 1.00 mm.

In one embodiment, the body 1002 is made from a nitinol tube having a thickness of 0.2 mm. If a spiral cut is made in the tube having a width of 0.2 mm thick, the cross section would reveal a square cross section. In one example, it is preferable to have the cut be greater than 0.2 mm, so that the distance between the wire turns is actually wider than deeper.

In FIG. 12, body 1000 includes one portion 1004 that is expanded, and a second portion 1004 that has been twisted by the internal wire 1003 so that it has a much smaller diameter.

Reference is now made to FIGS. 13A-13E, which are illustrations of a method of using system 10 within a vessel, in accordance with embodiments of the present invention.

Figure 13A:
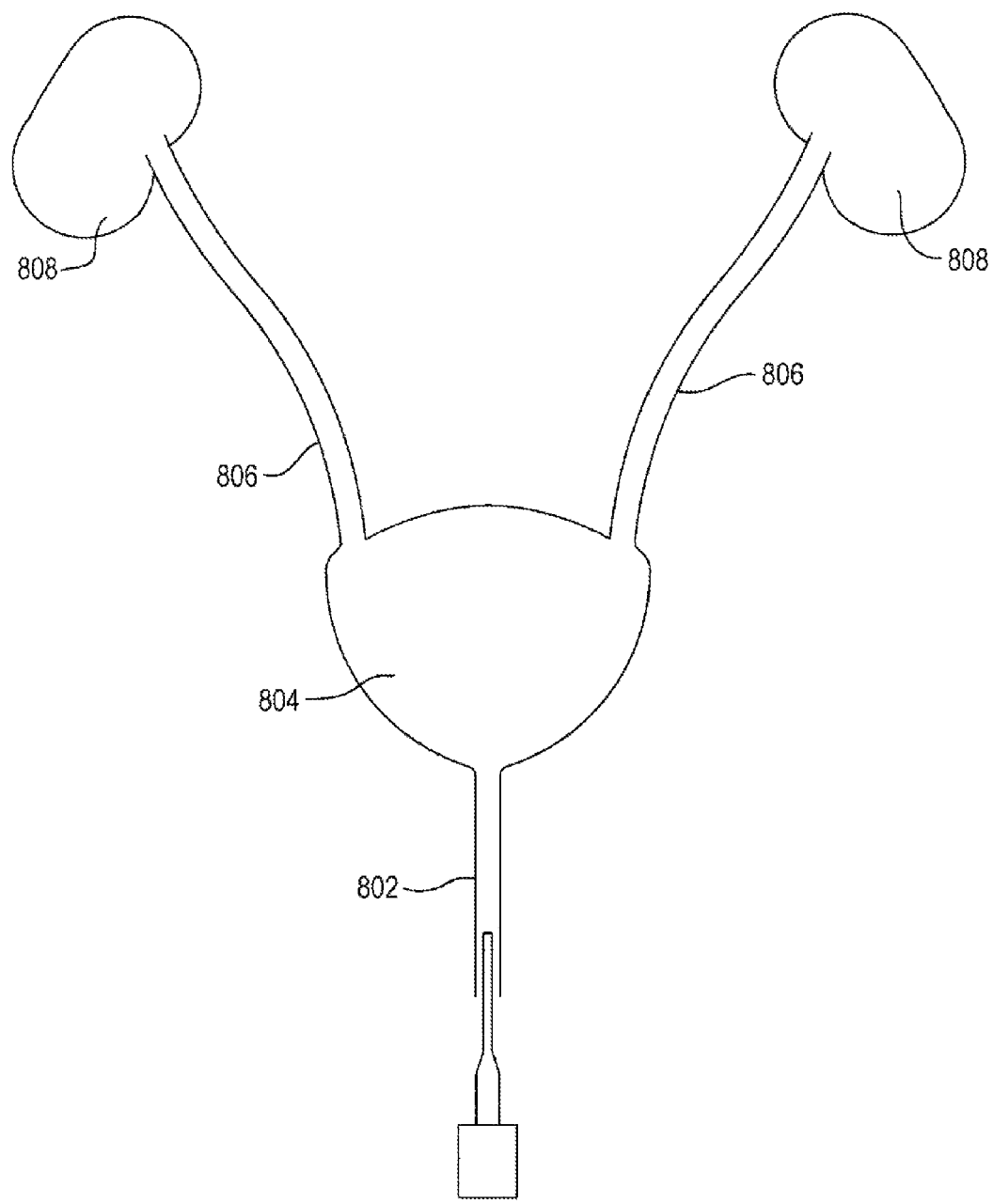
FIGS. 13A-13E are schematic illustrations of the steps of a method of using the system of the present application. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.
Figure 13B:
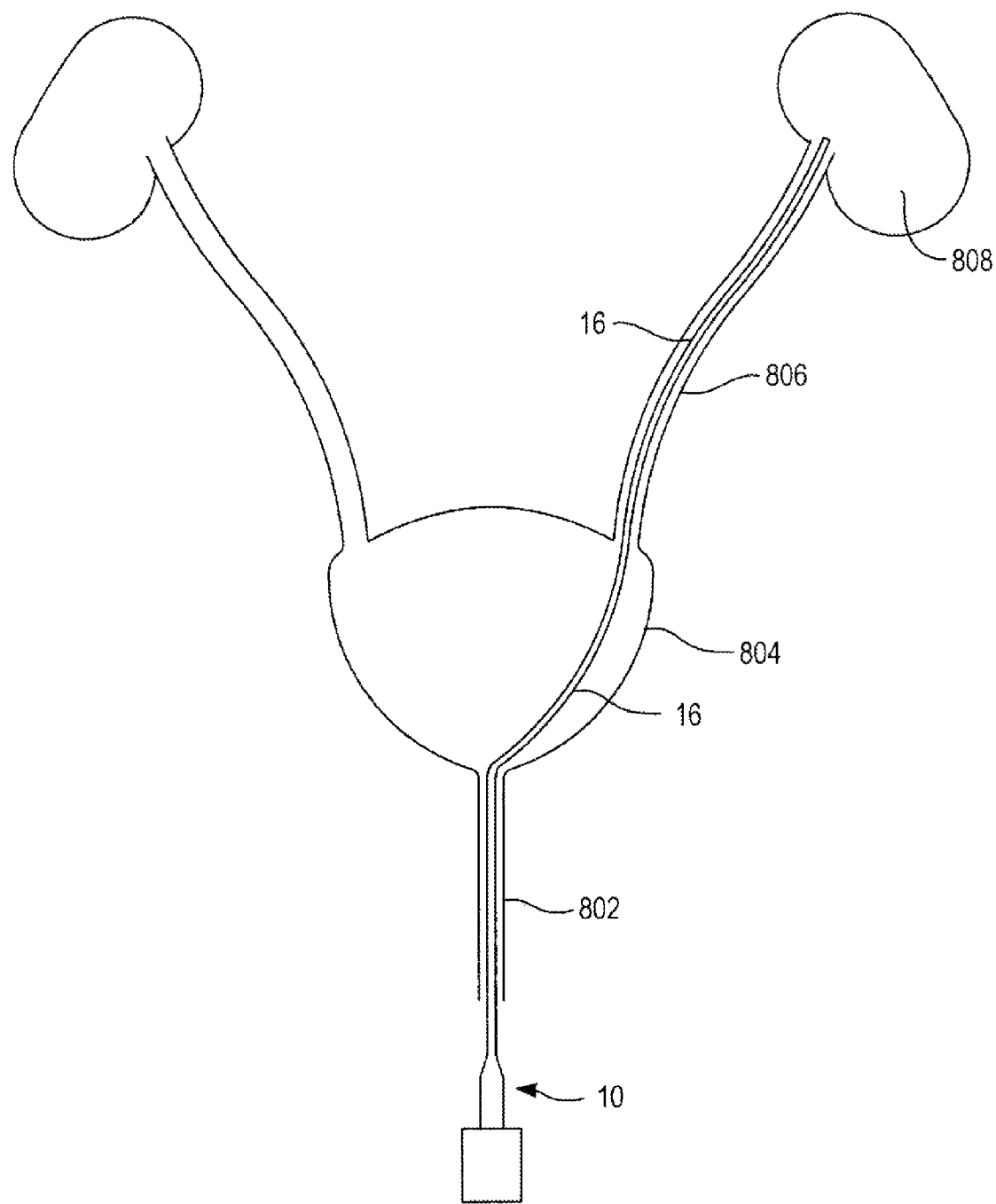
Figure 13C:
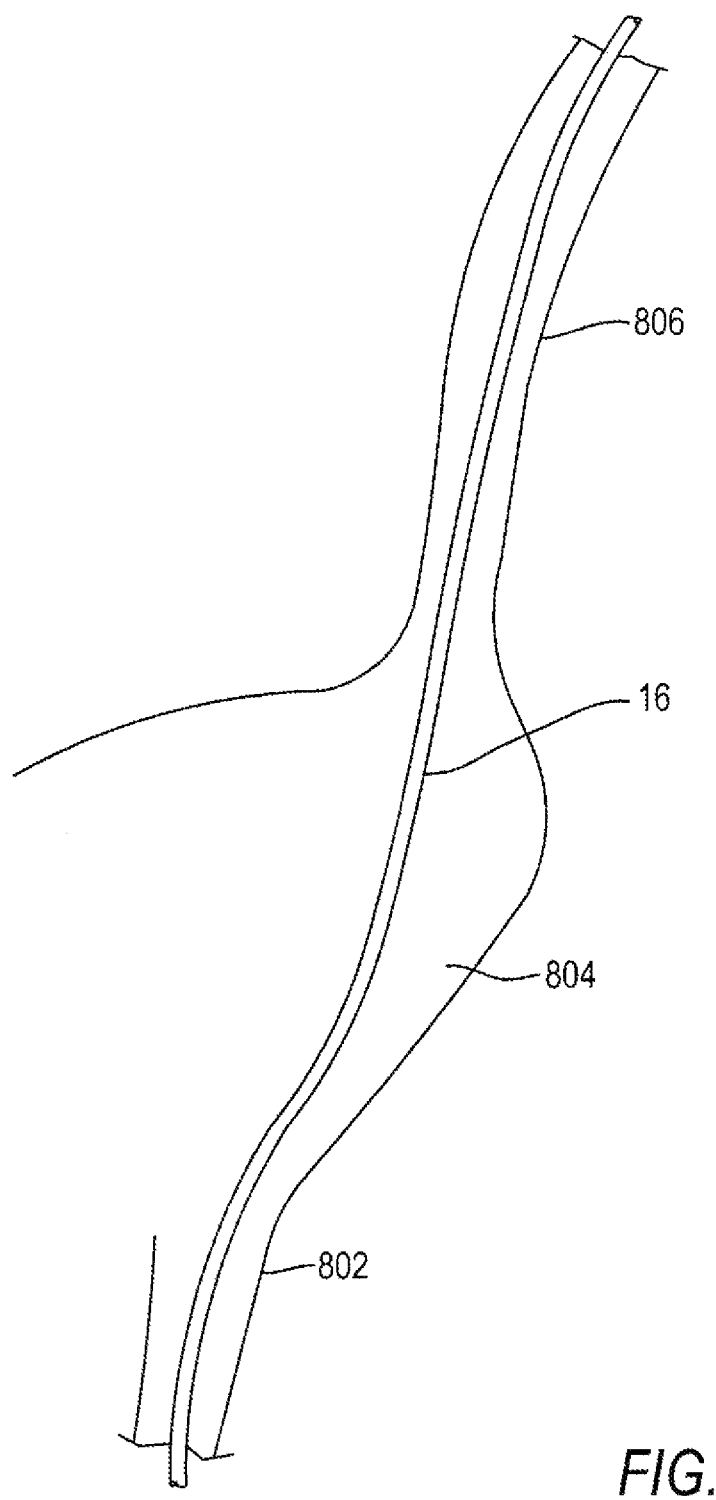
Figure 13D:
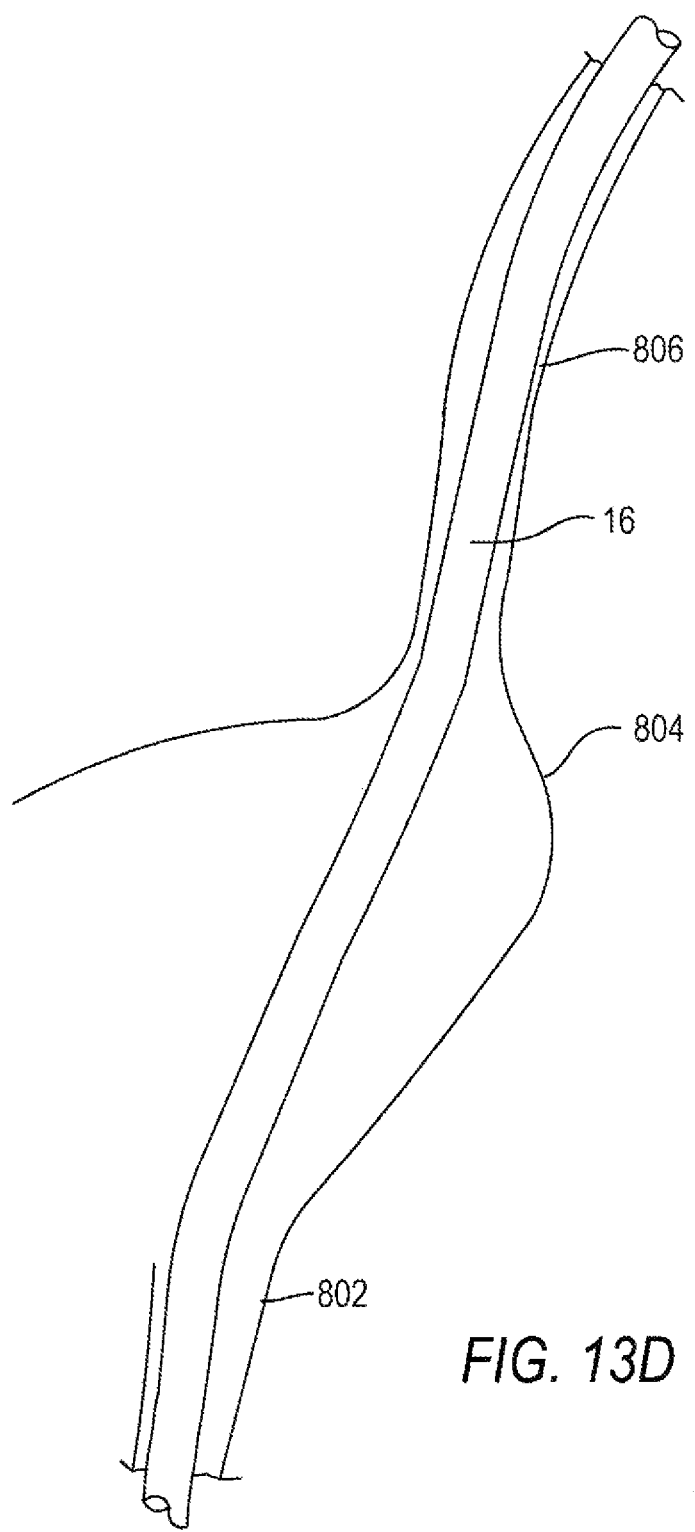
Figure 13E:
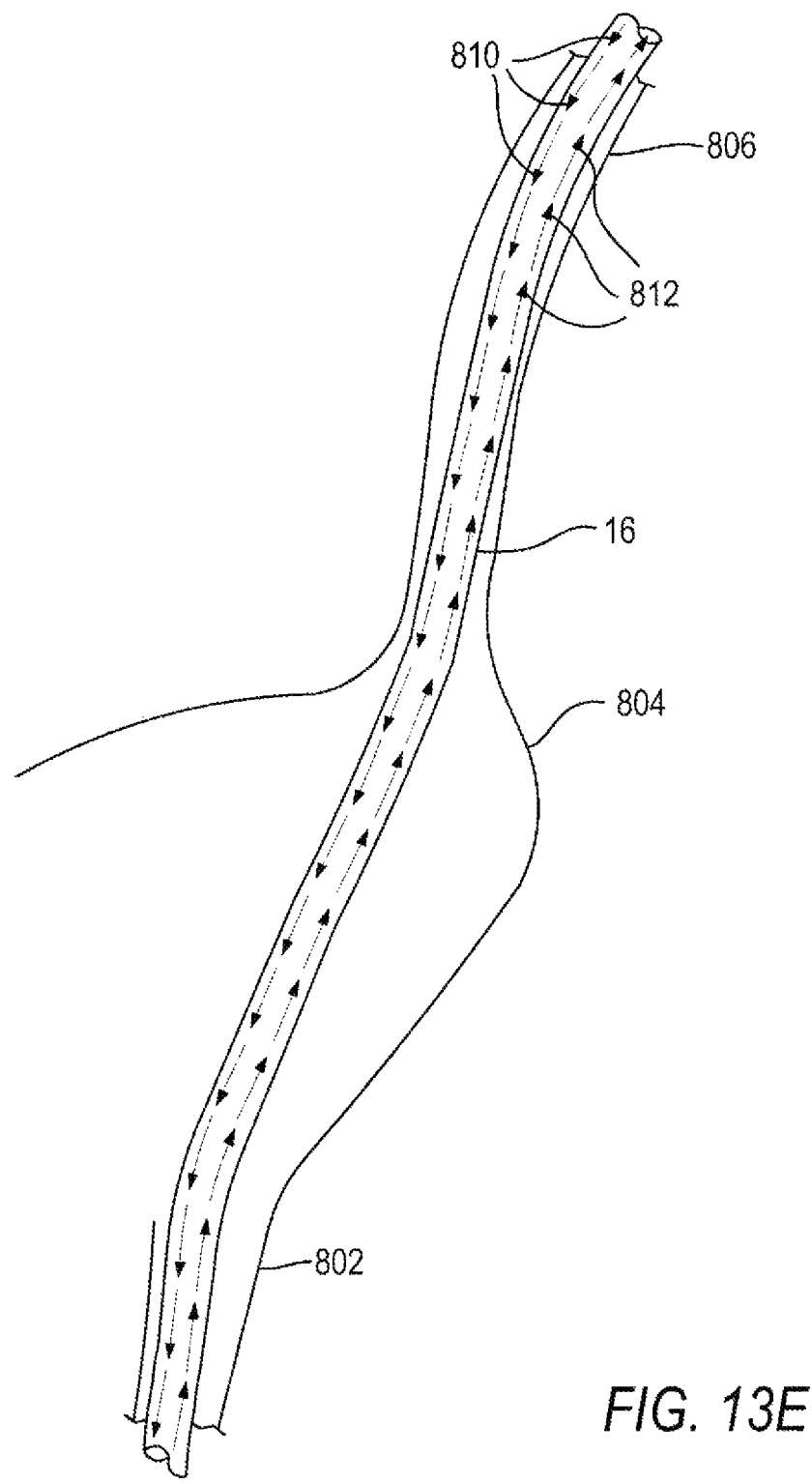

The application shown herein is a urology application. However, it should be readily apparent that system 10 may be designed for use in many different medical applications. Reference is now made to FIG. 13A, which shows system 10 as its being inserted into a urethra 802. Also shown are additional components of the urogenital system, including a bladder 804, ureters 806 and kidneys 808. Reference is now made to FIG. 13B, which is an illustration of system 10 after it has been advanced through the urogenital system and into a kidney 808. Expandable body 16 is in a contracted configuration, in accordance with, but not limited to, any of the embodiments disclosed herein. A closer view of contracted expandable body 16 is shown in FIG. 13C. System 10 is then expanded, as shown in FIG. 13D, to a larger diameter (or to several larger diameters at different sections along a length of system 10—not shown). It is a particular feature of the present invention that expansion of expandable body 16 may be done in a single step, without the need for multiple slow increases of diameter. Moreover, expansion of expandable body 16 is controlled by control mechanism 32, which a user may control via external control portion 31 from outside of the body using the various methods described herein. Next, items such as surgical instruments, fluids, drugs, etc. may be introduced through lumen of expandable body 16 into the vessel being treated (i.e. the kidney in the currently described method). This is shown schematically in FIG. 13E by use of arrows 810 for insertion of items and arrows 812 for removal of items from the vessel. Alternatively, or in addition to the above, items such as debris or kidney stones or other unwanted items may be removed through expandable body 16. After the procedure is done, expandable body 16 is contracted via control mechanism 32, and system 10 again resembles the configuration shown in FIGS. 13B and 13C. It should be noted that if the diameter of expandable body 16 is not as small after contraction as it had been before expansion, it still may be sufficient to safely remove expandable body 16 from the body. Finally, expandable body 16, in its contracted state, is removed from the body.

System 10 may be used in similar methods for intubation, vascular access or any other procedure which requires access to vessel in the body.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. An article comprising a tube having a normal external diameter and normal internal diameter comprising a coiled sheet of spring-like flexible material, the tube configured and adapted to be inserted in a lumen, wherein the normal external and internal diameters can be expanded when a hollow pipe of greater external diameter than the normal internal diameter of the tube is inserted in the tube, thereby causing the coiled sheath to uncoil and expand the internal diameter, and further including a removable tooth-like locking device adapted to lock the tube at an expanded diameter, wherein when the locking device is removed from the tube, the tube springs back to its normal external and internal diameter.

2. An article comprising a tube having a normal external diameter and normal internal diameter comprising a coiled sheet of spring-like flexible material, the tube configured and adapted to be inserted in a lumen, wherein the normal external and internal diameters can be expanded when a hollow pipe of greater external diameter than the normal internal diameter of the tube is inserted in the tube, thereby causing the coiled sheath to uncoil and expand the internal diameter, and further including a bar attached to spaced hinges which are in turn connected to arms, which are in turn attached to sliding bars running parallel to the inside of the tube and are equipped with stoppers which stop the bars from moving forward, adapted so that when the inner bar is pushed, the arms cause the sliding bars to move away from each other and cause the tube to expand to a larger internal and external diameter.

\* \* \* \* \*